US00PP12423P2

(12) United States Plant Patent
Small

(10) Patent No.: US PP12,423 P2
(45) Date of Patent: Feb. 26, 2002

(54) STRAWBERRY PLANT NAMED 'CAL GIANT 4'

(75) Inventor: David W. Small, Arroyo Grande, CA (US)

(73) Assignee: California Giant, Inc., Watsonville, CA (US)

( * ) Notice: Subject to any disclaimer, the term of this patent is extended or adjusted under 35 U.S.C. 154(b) by 52 days.

(21) Appl. No.: 09/613,179

(22) Filed: Jul. 10, 2000

(30) Foreign Application Priority Data

May 2, 2000 (EP) ..... 2000/0716

(51) Int. Cl.[7] ..... A01H 5/00
(52) U.S. Cl. ..... Plt./209
(58) Field of Search ..... Plt./209, 208

(56) References Cited

U.S. PATENT DOCUMENTS

| | | | | |
|---|---|---|---|---|
| PP5,262 | P | 7/1984 | Voth et al. | Plt./208 |
| PP5,266 | P | 7/1984 | Bringhurst et al. | Plt./209 |
| PP7,614 | P | 8/1991 | Bringhurst et al. | Plt./209 |
| PP7,615 | P | 8/1991 | Bringhurst et al. | Plt./209 |
| PP8,708 | P | 5/1994 | Voth et al. | Plt./209 |
| PP9,320 | P | 10/1995 | Small et al. | Plt./209 |
| PP10,451 | P | 6/1998 | Shaw | Plt./209 |
| PP10,461 | P | 6/1998 | Shaw | Plt./208 |
| PP10,960 | P | 6/1999 | Lopez | Plt./208 |
| PP10,982 | P | 6/1999 | D'Ercole et al. | Plt./208 |

*Primary Examiner*—Bruce R. Campell
*Assistant Examiner*—June Hwu
(74) *Attorney, Agent, or Firm*—David A. Farah; Sheldon & Mak

(57) ABSTRACT

A new and distinct variety of strawberry plant named 'Cal Giant 4' that produces equivalent yields of exceptionally high quality fruit in both fumigated and non-fumigated conditions, is tolerant of many common root, foliar, and fruit diseases and pests, produces exceptionally well-pollinated fruit in inclement conditions, maintains exceptional size and shape throughout the harvest season, and has exceptional flavor.

2 Drawing Sheets

CROSS-REFERENCE TO RELATED APPLICATION

This application takes priority from co-pending European Community Plant Protection Application No. 2000/0716, filed May 2, 2000, the contents of which are incorporated herein in their entirety.

BACKGROUND OF THE INVENTION

This new variety of strawberry, named 'Cal Giant 4,' resulted from a cross performed in 1994 between the proprietary plant designated 'A41' and the University of California variety 'Seascape' (U.S. Plant Pat. No. 7,614). The proprietary plant 'A41' was maintained exclusively for breeding purposes and was not released to growers and has not been the subject of an application for a plant patent in the United States.

'Cal Giant 4' was first selected as a seedling variety at the California Giant, Inc. Watsonville, Calif. breeding test plot in 1996 and has been propagated asexually by runners at Malin, Oreg. U.S. (42° N, 121.4° W). It was originally designated '49E31.' Asexual propagules from this original source have been placed in test plots in the fruiting areas of Oxnard, Santa Maria, and Watsonville, Calif., U.S. This propagation and testing has demonstrated that the combination of traits disclosed herein which characterize propagules of 'Cal Giant 4' are fixed and retained true to type through successive generations of asexual reproduction.

SUMMARY OF THE INVENTION

'Cal Giant 4' is a new and distinct strawberry variety characteristically different from any other strawberry variety. Among the characteristics that distinguish 'Cal Giant 4' are a combination of traits which include a strong everbearing tendency, very strong natural resistance to many pests and foliar, fruit and root diseases, and the production of a high number of very sweet fruit that are more uniformly sized and shaped than other commercial varieties. In addition, 'Cal Giant 4' produces equivalent yields of exceptionally high quality fruit in both fumigated and non-fumigated conditions. Fruit of 'Cal Giant 4' pollinates exceptionally well in inclement weather, allowing for continued production of well shaped, marketable fruit following cold, moist conditions.

BRIEF DESCRIPTION OF THE FIGURES

The accompanying color photograph show typical specimens of the new strawberry variety designated 'Cal Giant 4,' including fruit, foliage, and flower, as follows.

DETAILED BOTANICAL DESCRIPTION OF THE NEW VARIETY

Color terminology used herein is in accordance with the PANTONE® Color Formula Guide 1000 and the PANTONE® Formula Guide, as given below (Pantone Inc., 590 Commerce Boulevard, Carlstadt, N.J. U.S. 07072-3098). The color descriptions and color illustrations are as nearly true as is reasonably possible. However, it is understood that both color and other phenotypic expressions described herein may vary from plant to plant with differences in growth, environment and cultural conditions, without any change in the genotype of the variety 'Cal Giant 4.'

Unless specified otherwise, the 'Cal Giant 4' plants described below are nine months old.

Botanical Classification and Parentage

'Cal Giant 4' is a member of the genus Fragaria and species *ananassa.* It is a cross between proprietary variety 'A41' and University of California variety 'Seascape.' 'Cal Giant 4' is distinguished from its parents in that 'Cal Giant 4' is more compact, has darker foliage and greater resistance to soilborne and foliar diseases. Additionally, the fruit of 'Cal Giant 4' is more uniformly conic, has better size retention from the primary through teritary fruit and is more strongly day-neutral than either of its parents.

Physical Description

Figure 1:
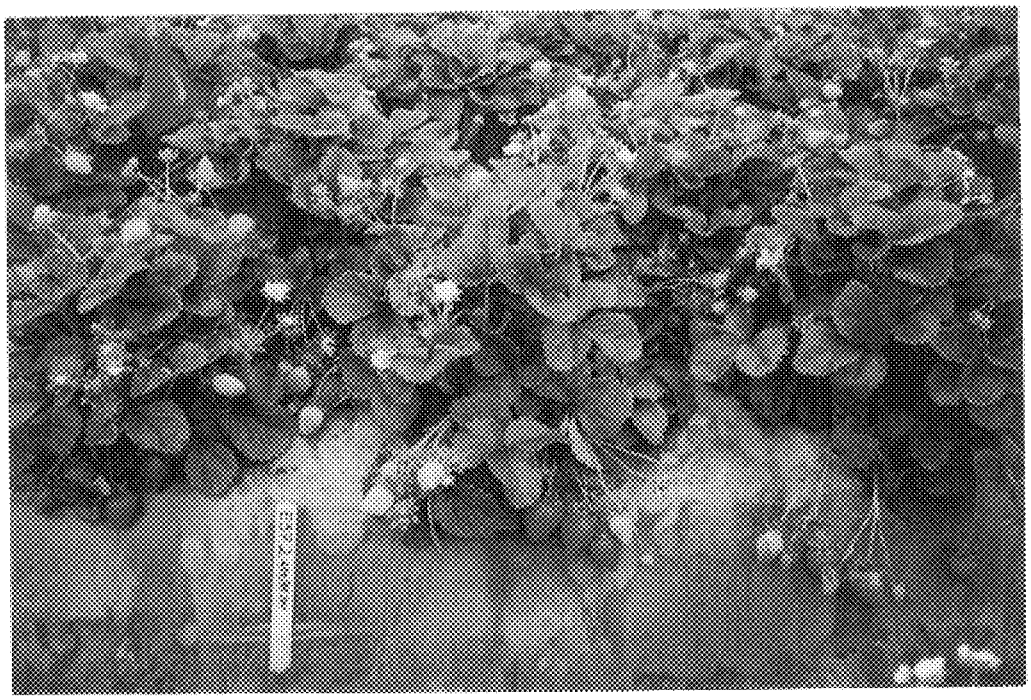
FIG. 1 is a color photograph taken in Santa Maria, Calif. on Jun. 19, 1998 showing typical plant architecture, flowering and fruiting characteristics of plants grown in a standard, fumigated cultural system.
Figure 2:
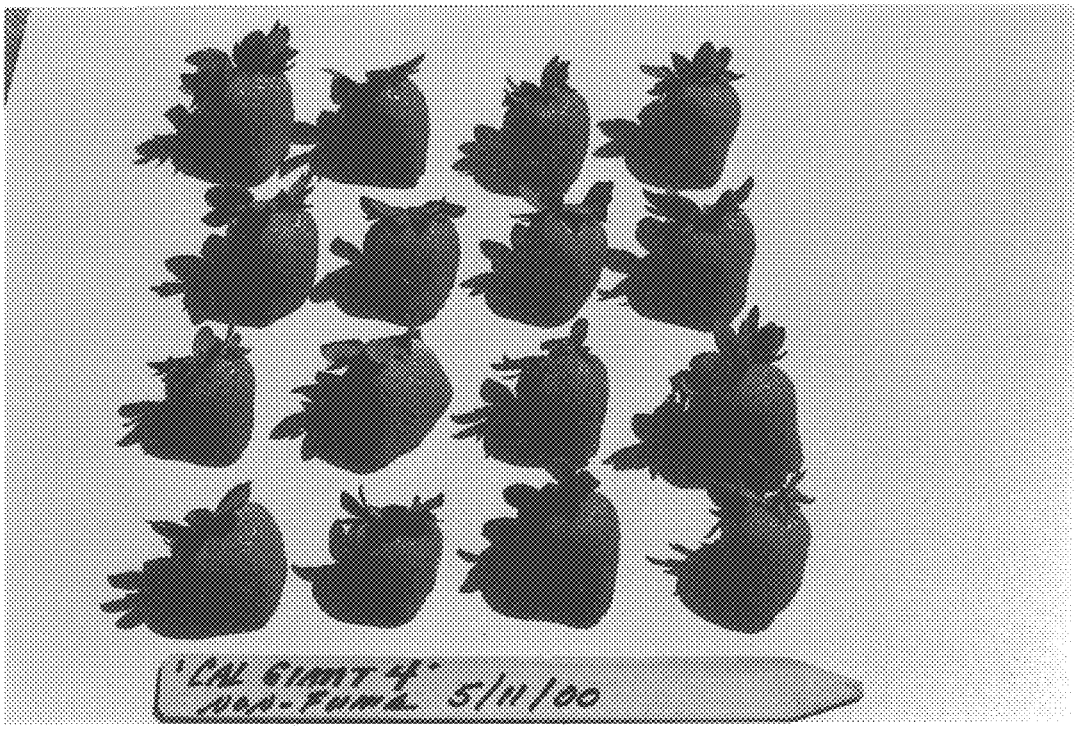
FIG. 2 is a color photograph showing typical fruit of plants grown in a non-fumigated cultural system.

Referring now to FIG. 1, there is shown a color photograph taken on Jun. 19, 1998 showing the general plant architectuure, flowering and fruiting characteristics of plants grown in a standard, fumigated, cultural system. Referring now to FIG. 2, there is shown a color photograph showing typical fruit of plants grown in a non-fumigated cultural system. As can be seen, fruiting plant of the 'Cal Giant 4' grow in a semi-erect to an erect habit. 'Cal Giant 4' plants are significantly more dense and turgid than 'Catalina' plants (U.S. Plant Pat. No. 9,320).

As can be seen further in FIG. 1, the blooms and fruit of 'Cal Giant 4' develop well away from the plant, advantageously easing harvest and allowing for good ventilation that reduces the incidence of fruit diseases. Inflorescence length is shorter than 'Catalina.' Mid-season inflorescence length, from the crown to the tip of the inflorescence, ranges from 31.0 cm to 39.3 cm, with an average length of 35.64 cm. Mid-season inflorescence length, from the crown to the tip of the primary fruit ranges from 30.1 cm to 43.1 cm, with an average length of 37.02 cm.

Early in the season, the pedicel splits from the peduncle inside the crown with single pedicels arising from the crown. As the season progresses, splitting of the pedicel from the peduncle occurs above the crown, forming the "multiple-hand."

Mid-season length of the peduncle from the crown to the point of pedicle connection ranges from 13.7 cm to 30.2 cm, with an average length of 24.75 cm. Mid-season peduncle diameter ranges from 2.5 mm to 5.7 mm, with an average diameter of 3.92 mm. The peduncle and pedicel are smooth, moderately pubescent, with pubescence measuring 1.5 mm in length and standing perpendicular to the peduncle and pedicel.

'Cal Giant 4' exhibits winged paired stipules at the base of the inflorescence. The length of these stipules ranges from 2.8 cm to 4.5 cm, with an average length of 3.64 cm.

The leaves of 'Cal Giant 4' are exceptionally strong and healthy with new leaves appearing above the existing canopy throughout the growing season. The leaves of 'Cal Giant 4' are rugose, flat, orbicular in shape with a dentate leaf margin, a rounded leaf apice, and a rounded, slightly cuneate leaf base. The leaves have a shiny, waxy cuticle. The number of serrations per older leaflet ranges from 16 to 23, averaging 19.25 serrations per leaflet. The number of serrations per younger leaflet ranges from 15 to 24, averaging 18.5 serrations per leaflet. The thickness of both the older and newer leaves range from 0.2 mm to 0.4 mm. The average thickness of the older leaves is 0.31 mm and the average thickness for the newer leaves is 0.28 mm.

'Cal Giant 4' plants exhibit an insignificant number of bract leaves. The presence or absence of bract leaves and their size do not appear to be related to the stage of development of the leaves or to the size of the plant. Further, 'Cal Giant 4' leaf petioles exhibit very spare tomentum which, when present, measure 1 mm or less in length.

'Cal Giant 4' plants leaves and leaf petioles have the following measurements:

TABLE I

'Cal Giant 4' Plants Leaves and Leaf Petioles Measurements

| | Range | Average |
|---|---|---|
| older mid-season leaf petioles length | 14.5 cm to 20.5 cm | 17.95 cm |
| newer mid-season leaf petioles length | 19.5 cm to 24.5 cm | 22.9 cm |
| older trifoliate leaves height | 23 cm to 28 cm | 25.95 cm |
| newer trifoliate leaves height | 27.5 cm to 35 cm | 30.675 cm |
| older trifoliate leaves width | 13.5 cm to 19 cm | 15.26 cm |
| newer trifoliate leaves width | 10 cm to 15.8 cm | 13.55 cm |
| older petiole mid-point diameter | 3 mm to 4.5 mm | 3.51 mm |
| newer petiole mid-point diameter | 2.4 mm to 4.1 mm | 2.95 mm |

'Cal Giant 4' mid-season inflorescence length averages 35.64 cm from the crown to the apice of the primary fruit. The buds, blooms and fruit are initially borne on single stems with branching occurring in the crown of the plant. Mid-season buds, blooms, and fruit are borne on dichasium cyme.

'Cal Giant 4' plant leaves tend to be dark green in color, much darker than 'Catalina.' Visual comparisons of 'Cal Giant 4' leaf color to 'Catalina,' 'Camarosa' (U.S. Plant Pat. No. 8,708), and 'Chandler' (U.S. Plant Pat. No. 5,262) leaf colors were made using the PANTONE® Color Formula Guide 1000 (Pantone Inc., 590 Commerce Boulevard, N.J. U.S.A. 07072-3098) and the results are given in Table II, below.

The number of flower petals on the 'Cal Giant 4' blooms range from 5 to 8, averaging 6.35 petals per bloom. The petals are completely white, showing no tint of red. Petal diameter ranges from 2.6 cm to 3.5 cm, averaging 3.07 cm. The calyx is nonclasping, slightly rugose, mildly pubescent and can be slightly to moderately reflexed. The calyx inserts directly into the shoulder of the berry. The sepals alternatively adhere to the berry and reflex away from the berry. Calyces have an outer diameter on primary flowers from 2.6 cm to 4 cm, averaging 3.26 cm. Calyces have an inner diameter on secondary flowers of about 2.5 cm and an outer diameter on secondary flowers of about 3.6 cm. Stamen are three-tiered and range from 24 to 34 stamen per flower, averaging 27.3 stamen. Filament length ranges from less than 1 mm to 3 mm. The flowers average 3.5 mm in diameter and their petals overlap.

The surface of the fruit of 'Cal Giant 4' is significantly smoother than other commercially grown varieties such as 'Aromas' (U.S. Plant Pat. No. 10,451), 'Catalina,' 'Camarosa,' and 'Diamante,' (U.S. Plant Pat. No. 10,435). Both primary and secondary fruit of 'Cal Giant 4' are approximately the same. The fruit tends to be very conic, with occasional fruit that is longitudinally wedge shaped. 'Cal Giant 4' fruit is highly glossed. Seeds are even with the skin. The immature seed color is 584U and the mature seed color is 1955C, using the PANTONE® Formula Guide. The ratio of the width of the fruit to the length of the fruit of the conic berries is 3.8:4.4 (0.86); the ratio of the width of the fruit to the length of the fruit of the wedge shaped berries is 4.1:4.8 (0.86).

'Cal Giant 4' produces a much higher level of well-shaped, unblemished fruit than 'Aromas,' 'Catalina,' 'Camarosa,' 'Chandler,' and 'Diamante.' Advantageously, the difference in fruit size between primary, secondary, and tertiary fruit is significantly less than the difference in 'Aromas,' 'Catalina,' 'Camarosa,' and 'Chandler.'

The skin and flesh of 'Cal Giant 4' are firmer than 'Catalina,' 'Chandler,' and 'Diamante.' The exterior and interior fruit color is slightly darker than that of 'Aromas,' 'Camarosa' and 'Diamante.' 'Cal Giant 4' fruit flesh displays good color saturation and the interior color substantially matches the exterior color. Visual comparisions of 'Cal Giant 4' fruit color were made to the fruit color of 'Catalina,' 'Camarosa,' and 'Chandler' using the PANTONE® Color Formula Guide 1000, except for the internal fruit color of 'Cal Giant 4' that was made using the PANTONE® Color Formula Guide 1000, and the results are given in Table II, below.

TABLE II

Visual Comparison of 'Cal Giant 4' Leaf and Fruit Color to 'Catalina,' 'Camarosa,' and 'Chandler' Leaf and Fruit Color

| | Adaxial Leaf | Abaxial Leaf | External Fruit | Internal Fruit |
|---|---|---|---|---|
| 'Cal Giant 4' | 576U | 577U | 1797U | 186C |
| 'Camarosa' | 349C | 348U | 193C | 185C |
| 'Catalina' | 343C | 348U–356U | 193C | 185C |
| 'Chandler' | 3435C | 339U | 186C | 179C |

Additionally, 'Cal Giant 4' plants display the following colors using the PANTONE® Formula Guide: peduncle 383U; petiole 383U; bract, adaxial 357U; bract, abaxial 370U; calyx, adaxial 7496C; and calyx, abaxial 369C.

The soluble solid content of 'Cal Giant 4' fruit was determined (9.75%) utilizing a TY' MUP® 11-520-0 ATC Refractometer. 'Cal Giant 4' has excellent flavor and is highly aromatic.

Protein Characteristics

The isoenzyme banding patterns of 'Cal Giant 4' as determined by gel electrophoresis is compared with the isoenzyme content of other strawberry varities in Table III, below.

TABLE III

Comparisons of 'Cal Giant 4' Isoenzyme Banding Patterns with the Isoenzyme Banding Patterns of 'Aromas,' 'Catalina,' 'Diamante' and 'Gaviota'

| | Phosphoglucose-isomerase (PG1) | Leucine Aminopeptidase (LAP) | Phospho-glucomutase (PGM) |
|---|---|---|---|
| 'Cal Giant 4' | A2 | B3 | C4 |
| 'Aromas,' | A4 | B3 | C2 |
| 'Catalina' | A4 | B3 | C4 |
| 'Diamante' | A4 | B3 | C2 |
| 'Gaviota' | A2 | B3 | C1 |

Resistance to Diseases and Pests

Of particular significance, 'Cal Giant 4' produces equivalent plants and equivalent yields of exceptionally high quality fruit in both fumigated and non-fumigated conditions. 'Cal Giant 4' displays excellent tolerance to *Verticillium wilt*, Phytophthora spp., *Rhizoctonia fragariae*, and Pythium spp. In non-fumigated conditions 'Cal Giant 4' is more vigorous, and healthy, shows greater resistance or tolerance to soil borne diseases, and is more fruitful than 'Aromas,' 'Camarosa,' 'Diamante,' and 'Gaviota' (U.S. Plant Pat. No. 10,461). Further, 'Cal Giant 4' displays significant tolerance to Tetranychus sp., appearing completely unaffected when highly infested.

Productivity Characteristics

'Cal Giant 4' pollinates exceptionally well in highly inclement conditions, and between the temperature range of −7° C. and 43° C., thus facilitating significant early season production with few fruit being thrown away due to poor pollination. 'Cal Giant 4' allows for fresh market harvesting throughout the entire fruiting season (March through October). The fruit has been successfully stored at 1° C. for 96 hours than at 20° C. for an additional 24 hours.

'Cal Giant 4' is very high yielding, coming into production shortly after 'Camarosa,' with 'Catalina,' and ahead of 'Aromas' and 'Diamante.' 'Cal Giant 4' produces fruit throughout the summer and well into the autumn months, and has shown good tolerance to heat, high pH and salt level stress. Due to the very high percentage of commercially acceptable fruit and very low percentage of culled fruit the 'Cal Giant 4' harvests very efficiently. Additionally, the character of 'Cal Giant 4' fruit allows for harvesting high quality processing fruit.

What is claimed:

1. A new and distinct strawberry plant designated 'Cal Giant 4' as herein described and illustrated.

* * * * *